US009580368B2

(12) United States Patent
Chen et al.

(10) Patent No.: US 9,580,368 B2
(45) Date of Patent: Feb. 28, 2017

(54) DEHYDROGENATION PROCESS

(75) Inventors: Tan-Jen Chen, Kingwood, TX (US); Jihad Mohammed Dakka, Whitehouse Station, NJ (US); Terry Eugene Helton, Bethlehem, PA (US); Francisco Manuel Benitez, Cypress, TX (US); Charles Morris Smith, Houston, TX (US); Lorenzo Cophard DeCaul, Langhorne, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 292 days.

(21) Appl. No.: 14/006,338

(22) PCT Filed: Dec. 2, 2011

(86) PCT No.: PCT/US2011/063112
§ 371 (c)(1),
(2), (4) Date: Dec. 2, 2013

(87) PCT Pub. No.: WO2012/134552
PCT Pub. Date: Oct. 4, 2012

(65) Prior Publication Data
US 2014/0323782 A1   Oct. 30, 2014

Related U.S. Application Data

(60) Provisional application No. 61/468,298, filed on Mar. 28, 2011.

(30) Foreign Application Priority Data

May 19, 2011 (EP) ..................................... 11166684

(51) Int. Cl.
C07C 5/367   (2006.01)
C07C 5/32    (2006.01)

(52) U.S. Cl.
CPC .............. *C07C 5/367* (2013.01); *C07C 5/325* (2013.01); *C07C 2523/14* (2013.01); *C07C 2523/42* (2013.01); *C07C 2523/62* (2013.01)

(58) Field of Classification Search
USPC ....... 585/320, 315, 318, 316, 314, 319, 323, 585/431
See application file for complete search history.

(56) References Cited

U.S. PATENT DOCUMENTS

| | | |
|---|---|---|
| 2,620,314 A | 12/1952 | Hoekstra |
| 3,308,069 A | 3/1967 | Wadlinger et al. |
| 3,354,078 A | 11/1967 | Miale et al. |
| 3,358,044 A | 12/1967 | Russell et al. |
| 3,412,167 A | 11/1968 | Lewis |
| 3,514,492 A | 5/1970 | Juguin et al. |
| 3,519,575 A | 7/1970 | Bozik et al. |
| 3,534,110 A | 10/1970 | Juguin et al. |
| 3,534,116 A | 10/1970 | Fuller |
| 3,580,970 A | 5/1971 | Swift |
| 3,691,102 A | 9/1972 | Swift |
| 3,761,428 A | 9/1973 | Sugier et al. |
| RE28,341 E | 2/1975 | Wadlinger et al. |
| 3,864,284 A | 2/1975 | Clippinger et al. |
| 3,909,451 A | 9/1975 | Wilhelm |
| 3,962,362 A | 6/1976 | Suggitt |
| 4,008,180 A | 2/1977 | Rausch |
| 4,048,245 A * | 9/1977 | Pollitzer .............. B01J 23/8966 502/227 |
| 4,094,918 A | 6/1978 | Murtha et al. |
| 4,122,125 A | 10/1978 | Murtha et al. |
| 4,130,597 A | 12/1978 | Wilhelm |
| 4,133,839 A | 1/1979 | Hayes |
| 4,177,165 A | 12/1979 | Murtha et al. |
| 4,206,082 A | 6/1980 | Murtha et al. |
| 4,417,076 A | 11/1983 | Rozovsky et al. |
| 4,439,409 A | 3/1984 | Puppe et al. |
| 4,501,926 A | 2/1985 | LaPierre et al. |
| 4,542,248 A | 9/1985 | Lucien |
| 4,826,667 A | 5/1989 | Zones et al. |
| 4,870,217 A | 9/1989 | Knifton |
| 4,891,458 A | 1/1990 | Innes et al. |
| 4,929,762 A | 5/1990 | Matsunaga et al. |
| 4,933,507 A | 6/1990 | Inoki et al. |

(Continued)

FOREIGN PATENT DOCUMENTS

| | | |
|---|---|---|
| CS | 177505 | 7/1977 |
| EP | 0 293 032 | 11/1988 |

(Continued)

OTHER PUBLICATIONS

Borodina et al., "Hydroalkylation of Benzene and Ethylbenzene Over Metal Containing Zeolite Catalysts", Microporous and Mesoporous Materials, 2007, vol. 105, No. 1-2, pp. 181-188.

Du et al., "The Chemistry of Selective Ring-Opening Catalysts", Applied Catalysis A: General, 2005, vol. 294, No. 1, pp. 1-21.

Galperin et al., "Effect of Support Acid—Basic Properties on Activity and Selectivity of Pt Catalysts in Reaction of Methylcyclopentane Ring Opening", Applied Catalysis A: General, 2003, vol. 239, pp. 297-304.

Gault, "Mechanisms of Skeletal Isomerization of Hydrocarbons on Metals", Advances in Catalysis, 1981, vol. 30, pp. 1-95.

Gonzales-Cortes et al., "Tuning the Ring-Opening Reaction of 1,3-dimethylcyclohexane with the Addition of Potassium Over Ir-Containing Catalysts", Chemical Engineering Journal, 2008, vol. 139, pp. 147-156.

(Continued)

*Primary Examiner* — Sharon Pregler

(57) ABSTRACT

Disclosed herein is a process for dehydrogenating a saturated cyclic hydrocarbon and/or 5-membered ring compound with a dehydrogenation catalyst. The dehydrogenation catalyst comprises: (i) 0.05 wt % to 5 wt % of a metal selected from Group 14 of the Periodic Table of Elements; and (ii) 0.1 wt % to 10 wt % of a metal selected from Groups 6 to 10 of the Periodic Table of Elements. The process is conducted under dehydrogenation conditions effective to dehydrogenate at least a portion saturated cyclic hydrocarbon and/or 5-membered ring compound.

17 Claims, 1 Drawing Sheet

(56) References Cited

U.S. PATENT DOCUMENTS

| | | | |
|---|---|---|---|
| 4,954,325 | A | 9/1990 | Rubin et al. |
| 5,053,571 | A | 10/1991 | Makkee |
| 5,236,575 | A | 8/1993 | Bennett et al. |
| 5,250,277 | A | 10/1993 | Kresge et al. |
| 5,256,348 | A | 10/1993 | Waller |
| 5,362,697 | A | 11/1994 | Fung et al. |
| 5,811,624 | A | 9/1998 | Hantzer et al. |
| 5,906,729 | A | 5/1999 | Chou |
| 6,037,513 | A | 3/2000 | Chang et al. |
| 6,049,018 | A | 4/2000 | Calabro et al. |
| 6,077,498 | A | 6/2000 | Diaz Cabañas et al. |
| 6,187,984 | B1 | 2/2001 | Wu et al. |
| 6,201,157 | B1 | 3/2001 | Keenan |
| 6,489,529 | B1 | 12/2002 | Cheng et al. |
| 6,720,462 | B2 | 4/2004 | Kuhnle et al. |
| 6,730,625 | B1 | 5/2004 | Chang et al. |
| 6,756,030 | B1 | 6/2004 | Rohde et al. |
| 7,285,685 | B2 | 10/2007 | Walsdorff et al. |
| 7,563,358 | B2 | 7/2009 | Stavens et al. |
| 7,579,511 | B1 * | 8/2009 | Dakka .................. C07C 2/74 585/314 |
| 7,605,107 | B2 | 10/2009 | Soled et al. |
| 2003/0083527 | A1 | 5/2003 | Kuhnle et al. |
| 2006/0166809 | A1 | 7/2006 | Malek et al. |
| 2007/0032681 | A1 | 2/2007 | Walsdorff et al. |
| 2008/0051618 | A1 | 2/2008 | Kim et al. |
| 2008/0262281 | A1 | 10/2008 | Walsdorff et al. |
| 2011/0021844 | A1 | 1/2011 | Dakka et al. |
| 2011/0105805 | A1 | 5/2011 | Buchanan et al. |
| 2014/0066663 | A1 * | 3/2014 | Dakka .................. B01J 23/626 568/799 |
| 2014/0323782 | A1 | 10/2014 | Chen et al. |

FOREIGN PATENT DOCUMENTS

| | | |
|---|---|---|
| EP | 0 323 192 | 7/1989 |
| GB | 720064 | 12/1954 |
| GB | 1454717 | 11/1976 |
| JP | 54-099788 | 8/1979 |
| JP | H02-188542 | 7/1990 |
| JP | 2004-196638 | 7/2004 |
| WO | WO91/06616 | 5/1991 |
| WO | WO 97/17290 | 5/1997 |
| WO | WO 2005/009937 | 2/2005 |
| WO | 2006/078240 | 7/2006 |
| WO | WO 2007/084440 | 7/2007 |
| WO | WO 2009/025939 | 2/2009 |
| WO | 2009/131769 | 10/2009 |
| WO | WO 2009/128984 | 10/2009 |
| WO | WO 2010/024975 | 3/2010 |
| WO | 2010/042261 | 4/2010 |
| WO | 2011/096989 | 8/2011 |
| WO | 2011/096990 | 8/2011 |
| WO | 2011/096991 | 8/2011 |
| WO | 2011/096992 | 8/2011 |
| WO | 2011/096993 | 8/2011 |
| WO | 2011/096994 | 8/2011 |
| WO | 2011/096995 | 8/2011 |
| WO | 2011/096996 | 8/2011 |
| WO | 2011/096997 | 8/2011 |
| WO | 2011/096998 | 8/2011 |
| WO | 2011/096999 | 8/2011 |
| WO | WO 2011/162850 | 12/2011 |
| WO | 2012/050665 | 4/2012 |
| WO | 2012/082407 | 6/2012 |

OTHER PUBLICATIONS

Koel et al., "*Thermochemistry of the Selective Dehydrogenation of Cyclohexane to Benzene on Pt Surfaces*", Journal of Molecular Catalysis: A Chemical, 1998, vol. 131, pp. 39-53.

Smirniotis et al., "*Comparison Between Zeolite β and γ-Al$_2$O$_3$ Supported Pt for Reforming Reactions*", Journal of Catalysis, 1993, vol. 140, pp. 526-542.

Smirniotis et al., "*Increased Aromatization in the Reforming of Mixtures of N-Hexane, Methylcyclopentane and Methylcyclohexane Over Composites of Pt/BaKL Zeolite with Pt/Beta or Pt/USY Zeolites*", Applied Catalysis A: General, 1995, vol. 123, No. 1, pp. 59-88.

Soled et al., "*Supported Metal Catalysts: Some Interesting New Leads in an Old Field*", Scientific Bases for the Preparation of Heterogeneous Catalysts, 2006, vol. 162, pp. 103-110.

Koshel et al. "*A Commercial Synthesis of Phenylcyclohexane ((PHCH)) by the Hydrodimerization of Benzene*", Neftekhimiya, 1977, vol. 17, pp. 705-709.—Translation.

Miale, "*Catalysis by Crystalline Aluminosilicates—IV. Attainable Catalytic Cracking Rate Constants, and Superactivity*", Journal of Catalysis, vol. 6, pp. 278-287, 1966.

Weisz, "*Superactive Crystalline Aluminosilicate Hydrocarbon Catalysts*", Journal of Catalysis, vol. 4, pp. 527-529, 1965.

Olson et al., "*Chemical and Physical Properties of the ZSM-5 Substitutional Series*", Journal of Catalysis, vol. 61, pp. 390-396, 1980.

Savostin et al., "The Addition of Tin to Platinum Alumina Catalysts", Order of Labor's Red Banner Institute of Catalysis, Siberian Dept., Academy of Sciences of the USSR, 1979, No. 1, pp. 18-21. (translation).

* cited by examiner

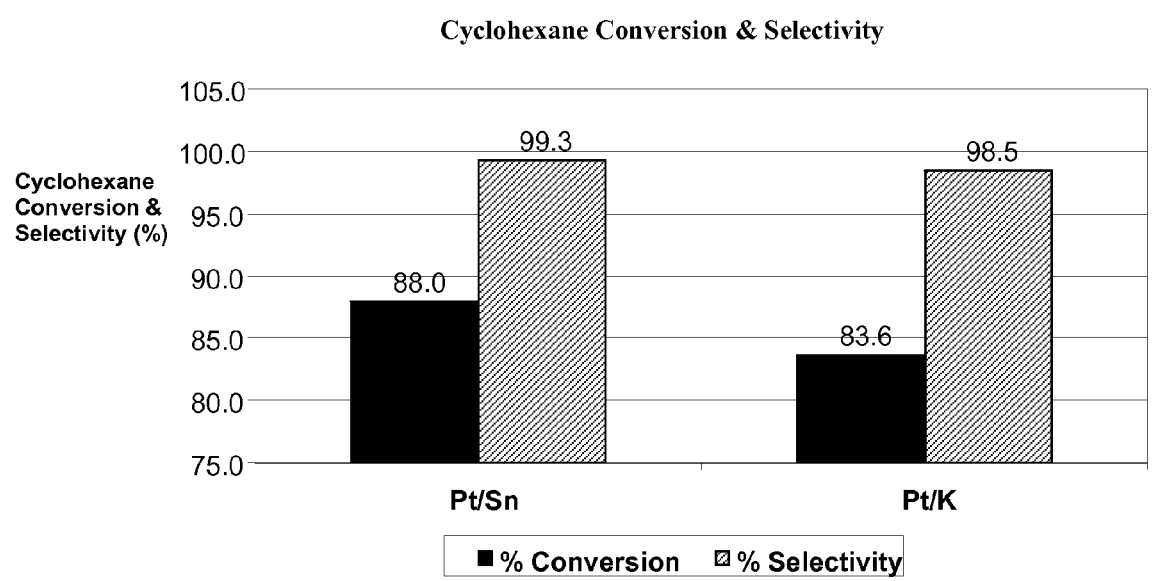

DEHYDROGENATION PROCESS

PRIORITY CLAIM TO RELATED APPLICATIONS

This application is a National Stage Application of International Application No. PCT/US2011/063112 filed Dec. 2, 2011, which claims priority to U.S. Provisional Application Ser. No. 61/468,298 filed Mar. 28, 2011, and European Application No. 11166684.8 filed May 19, 2011, the disclosures of which are fully incorporated herein by their reference.

CROSS REFERENCE TO RELATED APPLICATIONS

This patent application is related to U.S. Provisional Application Ser. No. 61/424,242, filed Dec. 17, 2010 and PCT Application Serial No. PCT/US2010/061041, filed Dec. 17, 2010.

FIELD

The present invention relates to a process for dehydrogenating saturated cyclic hydrocarbons such as cyclohexane and/or methylcyclopentane, and in particular, cyclohexane and methylcyclopentane produced during hydroalkylation of benzene to cyclohexylbenzene.

BACKGROUND

Cyclohexylbenzene can be produced from benzene by the process of hydroalkylation or reductive alkylation. In this process, benzene is heated with hydrogen in the presence of a catalyst such that the benzene undergoes partial hydrogenation to produce a reaction intermediate such as cyclohexene which then alkylates the benzene starting material. Thus, U.S. Pat. Nos. 4,094,918 and 4,177,165 disclose hydroalkylation of aromatic hydrocarbons over catalysts which comprise nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. In addition, U.S. Pat. No. 5,053,571 proposes the use of ruthenium and nickel supported on zeolite beta as the aromatic hydroalkylation catalyst. However, these earlier proposals for the hydroalkylation of benzene suffered from the problems that the selectivity to cyclohexylbenzene was low, particularly at economically viable benzene conversion rates, and that large quantities of unwanted by-products, particularly cyclohexane and methylcyclopentane, were produced.

More recently, U.S. Pat. No. 6,037,513 has disclosed that cyclohexylbenzene selectivity in the hydroalkylation of benzene can be improved by contacting the benzene and hydrogen with a bifunctional catalyst comprising at least one hydrogenation metal and a molecular sieve of the MCM-22 family. The hydrogenation metal is preferably selected from palladium, ruthenium, nickel, cobalt and mixtures thereof, and the contacting step is conducted at a temperature of 50 to 350° C., a pressure of 100 to 7000 kPa, a benzene to hydrogen molar ratio of 0.01 to 100 and a weight hourly space velocity (WHSV) of 0.01 to 100 hr$^{-1}$. The '513 patent discloses that the resultant cyclohexylbenzene can then be oxidized to the corresponding hydroperoxide and the peroxide decomposed to the desired phenol and cyclohexanone.

One disadvantage of this process is that it produces impurities such as cyclohexane and methylcyclopentane. These impurities represent loss of valuable benzene feed. Moreover, unless removed, these impurities will tend to build up in the system, thereby displacing increasing the production of undesirable by-products. Thus, a significant problem facing the commercial application of cyclohexylbenzene as a phenol precursor is removing the cyclohexane and methylcyclopentane impurities.

One solution to this problem is proposed in U.S. Pat. No. 7,579,511 which describes a process for making cyclohexylbenzene in which benzene undergoes hydroalkylation in the presence of a first catalyst to form a first effluent composition containing cyclohexylbenzene, cyclohexane, methylcyclopentane, and unreacted benzene. The first effluent composition is then separated into a cyclohexane/methylcyclopentane-rich composition, a benzene-rich composition, and a cyclohexylbenzene-rich composition and the cyclohexane/methylcyclopentane-rich composition is contacted with a second, low acidity, dehydrogenation catalyst to convert at least a portion of the cyclohexane to benzene and at least a portion of the methylcyclopentane to linear and/or branched paraffins and form a second effluent composition. The benzene-rich composition and the second effluent composition can then be recycled to the hydroalkylation step. However, one problem with this process is that cyclohexane and methylcyclopentane have similar boiling points to that of benzene so that their separation by conventional distillation is difficult.

Another solution is proposed in International Patent Publication No. WO2009/131769, in which benzene undergoes hydroalkylation in the presence of a first catalyst to produce a first effluent composition containing cyclohexylbenzene, cyclohexane, and unreacted benzene. The first effluent composition is then divided into a cyclohexylbenzene-rich composition and a $C_6$ product composition comprising cyclohexane and benzene. At least part of the $C_6$ product composition is then contacted with a second catalyst under dehydrogenation conditions to convert at least part of the cyclohexane to benzene and produce a second effluent composition which comprises benzene and hydrogen and which can be recycled to the hydroalkylation step.

Both of the processes disclosed in U.S. Pat. No. 7,579,511 and WO2009/131769 rely on the use of a dehydrogenation catalyst comprising a Group VIII metal on a porous inorganic support such as aluminum oxide, silicon oxide, titanium oxide, zirconium oxide, activated carbon and combinations thereof. However, in practice, such a dehydrogenation catalyst has only limited activity for the conversion of cyclohexane and/or methylcyclopentane and in some instances can undergo rapid aging. There is therefore a need for an improved catalyst for removing cyclohexane and methylcyclopentane from the benzene recycle compositions employed in benzene hydroalkylation processes. Conversion of cyclohexane is especially important since its boiling point is within 1° C. of that of benzene. Conversion of methylcyclopentane is also desired but less important than cyclohexane since there is a difference of nearly 9° C. in the boiling point of methylcyclopentane and benzene.

More recently, it was discovered that catalyst containing at least one dehydrogenation metal (e.g., platinum or palladium) and a Group 1 or Group 2 metal promoter (i.e., alkali metal or alkaline earth metals) can be used to dehydrogenate cyclohexane and/or methylcyclopentane. This process is described, for example, in PCT Application No. PCT/US2010/061041, which was filed on Dec. 17, 2010. However, dehydrogenation catalysts having further improved cyclohexane conversion and selectivity are needed.

That said, it has now been found that catalyst containing at least one dehydrogenation metal and a Group 14 metal (e.g., tin) have improved cyclohexane conversion and selectivity to benzene compared to dehydrogenation catalysts known in the art.

SUMMARY

In various embodiments, the invention relates to a dehydrogenation process that comprises contacting a composition comprising at least 50 wt % of an aromatic hydrocarbon and at least 0.1 wt % of a saturated cyclic hydrocarbon, the wt % based upon total weight of the composition, with a dehydrogenation catalyst. The dehydrogenation catalyst comprises: (i) 0.05 to 5 wt % of a metal selected from Group 14 of the Periodic Table of Elements; and (ii) 0.1 to 10 wt % of a metal selected from Groups 6 to 10 of the Periodic Table of Elements, the wt %s based upon total weight of the dehydrogenation catalyst.

Conveniently, the aromatic hydrocarbon is benzene and the saturated cyclic hydrocarbon is cyclohexane.

Conveniently, the metal selected from Group 14 of the Periodic Table of Elements is tin, and the metal selected from Groups 6 to 10 of the Periodic Table of Elements is platinum or palladium.

BRIEF DESCRIPTION OF THE DRAWINGS

FIG. 1 is a chart illustrating cyclohexane conversion and selectivity to benzene using a platinum/tin catalyst vs. a platinum/potassium catalyst.

DETAILED DESCRIPTION

Described herein is a process for dehydrogenating a composition, the process comprising a saturated cyclic hydrocarbon and/or a 5-membered ring compound with a dehydrogenation catalyst. The dehydrogenation catalyst comprises: (i) 0.05 wt % to 0.5 wt % of a metal selected from Group 14 of the Periodic Table of Elements; and (ii) 0.1 wt % to 2 wt % of a metal selected from Groups 6 to 10 of the Periodic Table of Elements. The dehydrogenation catalyst may further comprise a support. The process is conducted under dehydrogenation conditions effective to dehydrogenate at least a portion saturated cyclic hydrocarbon and/or 5-membered ring compound.

In various embodiments, the composition comprises at least 0.1 wt % of a saturated cyclic hydrocarbon, or at least 0.5 wt %, or least 1 wt %, or at least 5 wt %, at least 10 wt %, or at least 20 wt %, or at least 25 wt % of a saturated cyclic hydrocarbon, based upon total weight of the composition. In various embodiments, the saturated cyclic hydrocarbon is produced during a process for hydroalkylating benzene to form cyclohexylbenzene. For example, the saturated cyclic hydrocarbon may be cyclohexane.

The composition may further comprise at least 0.01 wt % of a 5-membered ring compound, or at least 0.05 wt %, or at least 0.1 wt %, or at least 0.3 wt %, or at least 0.5 wt % of the 5-membered ring compound, based upon total weight of the composition. The 5-membered ring compound may be produced during a process for hydroalkylating benzene to form cyclohexylbenzene. For example, the 5-membered ring compound may be methylcyclopentane.

The composition may further comprise at least 10 wt % of an aromatic hydrocarbon, or at least 20 wt %, or at least 30 wt %, or at least 40 wt %, or at least 50 wt %, or at least 60 wt %, or at least 70 wt %, or at least 80 wt % of an aromatic hydrocarbon, based upon total weight of the composition. In various embodiments, the aromatic hydrocarbon is produced during a process for hydroalkylating benzene to form cyclohexylbenzene. The aromatic hydrocarbon may be, for example, benzene.

The dehydrogenation catalyst employed in the dehydrogenation reaction comprises (i) a metal selected from Group 14 of the Periodic Table of Elements; and (ii) a metal selected from Groups 6 to 10 of the Periodic Table of Elements, the wt %s based upon total weight of the dehydrogenation catalyst. As used herein, the numbering scheme for the Periodic Table Groups disclosed herein is the New Notation provided on the inside cover of *Hawley's Condensed Chemical Dictionary* ($14^{th}$ Edition), by Richard J. Lewis.

Generally, the Group 14 metal is present in the dehydrogenation catalyst in an amount of at least 0.05 wt %, at least 0.1 wt %, at least 0.15 wt %, at least 0.2 wt %, at least 0.3 wt %, at least 0.4 wt %, or at least 0.5 wt %, or at least 1 wt %, or at least 5 wt % based upon total weight of the dehydrogenation catalyst. In one embodiment, the Group 14 metal is tin. In various embodiments, the Group 14 is present in an amount between 0.05 wt % and 5 wt %, or 0.05 wt % and 1 wt %, or 0.05 wt % and 0.5 wt % of the catalyst or between 0.1 wt % and 0.4 wt % of the catalyst or between 0.1 wt % and 0.3 wt %, or between about 0.15 wt % and 0.2 wt % of the dehydrogenation catalyst.

In addition, the catalyst comprises a metal selected from Groups 6 to 10 of the Periodic Table of Elements, such as platinum and/or palladium. Typically, the metal selected from Groups 6 to 10 of the Periodic Table of Elements is present in an amount between 0.05 and 10 wt % of the catalyst, such as between 0.1 wt % and 5 wt % of the catalyst or between 0.2 wt % and 2 wt % of the catalyst. In another embodiment, the Group 6 to 10 metal is present in an amount of at least 0.1 wt %, at least 0.2 wt %, at least 0.3 wt %, at least 0.4 wt %, at least 0.5 wt %, at least 0.6 wt %, at least 0.7 wt %, at least 0.8 wt %, at least 0.9 wt %, or at least 1.0 wt %. In various embodiments, the Group 6-10 metal is present in an amount between 0.1 wt % and 5 wt % of the catalyst, or between 0.1 wt % and 3 wt % of the catalyst, or between 0.1 wt % and 2 wt % of the catalyst, or between about 0.15 wt % and 1.5 wt % of the catalyst.

In various embodiments, the catalyst composition comprises less than 2 wt % of nickel, or <1 wt % nickel, or <0.5 wt % nickel, or less than 0.1 wt % nickel, or no nickel. In various embodiments, the catalyst composition comprises less than 2 wt % of cobalt, or <1 wt % cobalt, or <0.5 wt % cobalt, or less than 0.1 wt % cobalt, or no cobalt. In various embodiments, the catalyst composition is free or substantially free of ruthenium, rhodium, lead and/or germanium, and/or any other active elemental components.

In various embodiments, the ratio of the metal selected from Groups 6 to 10 of the Periodic Table of Elements to the metal selected from Group 14 of the Periodic Table of Elements (e.g., the Pt/Sn ratio) in the catalyst is greater than 0.5, or greater than 1, or greater than 1.5, or greater than 2.5, or greater than 2.7, or greater than 3, with a ratio of greater than 2.5 to 400, or 2.7 to 200, or 3 to 100 being preferred.

In various embodiments, the dehydrogenation catalyst further comprises a support. Conveniently, the dehydrogenation catalyst support is selected from the group consisting of silica, alumina, a silicate, an aluminosilicate, zirconia, carbon or carbon nanotubes. In various embodiments, the support comprises an inorganic oxide such as one or more of silicon dioxide, titanium dioxide, and zirconium dioxide. The support may or may not comprise a binder. Impurities that can be present in the catalyst support are, for example, sodium salts such as sodium silicate which can be present from anywhere from 0.01 wt % to 2 wt %. Suitable silica supports are described in, for example, PCT Pub. No. WO/2007084440 A1 filed on Jan. 12, 2007, and entitled "Silica Carriers" and is hereby incorporated by reference for this purpose.

It will be understood that the metal selected from Group 14 and/or the metal selected from Groups 6 to 10 of the Periodic Table of Elements may not be purely the elemental metal, but could, for example, be at least partly in another form, such as a salt, oxide, chloride, hydride, sulfide, carbonate, etc. For purposes of this application, the wt % of metal in the catalyst composition is calculated based upon the amount of metal used to form the component in the catalyst composition. Moreover, for purposes of determining wt %s of various components of the dehydrogenation catalyst, only that portion of the support that supports the Group 14 metal and/or the Group 6-10 metal is considered. For example, a catalyst composition made with 1.9 grams of tin chloride salt (1 gram of tin) and 22.29 grams of tetraammine platinum hydroxide solution (4.486 wt % Pt) that is supported on 98 grams of silicon dioxide contains 1 wt % of tin and 1 wt % Pt, based upon total weight of the catalyst composition.

The dehydrogenation catalyst is typically prepared by sequentially or simultaneously treating the support, such as by impregnation, with one or more liquid compositions comprising the Group 6-10 metal or a precursor thereof, the Group 14 metal or a precursor thereof and/or the optional inorganic base component or a precursor in a liquid carrier, such as water. An organic dispersant may be added to each liquid carrier to assist in uniform application of the metal component(s) to the support. Suitable organic dispersants include amino alcohols and amino acids, such as arginine. Generally, the organic dispersant is present in the liquid composition in an amount between 1 wt % and 20 wt % of the liquid composition.

In one preferred embodiment, the catalyst is prepared by sequential impregnation with the Group 14 metal component being applied to the support before the Group 6-10 metal component.

After treatment with the liquid composition, the support is heated in one or more stages, generally at a temperature of 100° C. to 700° C. for a time of 0.5 to 50 hours, to effect one or more of: (a) removal of the liquid carrier; (b) conversion of a metal component to a catalytically active form; and (c) decompose the organic dispersant. The heating may be conducted in an oxidizing atmosphere, such as air, or under reducing atmosphere conditions, such as hydrogen. After treatment with a liquid composition, the support is generally heated at a temperature of 200° C. to 500° C., such as 300° C. to 450° C., for a time of 1 to 10 hours.

In one embodiment, the dehydrogenation catalyst has an oxygen chemisorption value of greater than 5%, such as greater than 10%, for example greater than 15%, even greater than 20%, greater than 25%, or even greater than 30%. As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]*100%. The oxygen chemisorption values referred to herein are measured using the following technique. Oxygen chemisorption measurements are obtained using the Micromeritics ASAP 2010. Approximately 0.3 to 0.5 grams of catalyst are placed in the Micrometrics device. Under flowing helium, the catalyst is ramped from ambient (i.e., 18° C.) to 250° C. at a rate of 10° C. per minute and held for 5 minutes. After 5 minutes, the sample is placed under vacuum at 250° C. for 30 minutes. After 30 minutes of vacuum, the sample is cooled to 35° C. at 20° C. per minute and held for 5 minutes. The oxygen and hydrogen isotherm is collected in increments at 35° C. between 0.50 and 760 mm Hg. Extrapolation of the linear portion of this curve to zero pressure gives the total (i.e., combined) adsorption uptake.

Suitable conditions for the dehydrogenation step include a temperature of 100° C. to 1000° C., a pressure of atmospheric to 100 to 7000 kPa-gauge (kPag), a weight hourly space velocity of 0.2 $hr^{-1}$ to 50 $hr^{-1}$.

Preferably, the temperature of the dehydrogenation process is from 100° C. to 1000° C.; from 100° C. to 800° C.; from 150° C. to 600° C.; from 200° C. to 550° C. In other embodiments, the temperature lower limit may be 100° C.; 150° C.; 200° C.; 250° C.; 300° C.; 350° C.; 400° C.; 450° C.; and 500° C.; and the upper limit temperature may be 1000° C.; 950° C.; 900° C.; 850° C.; 800° C.; 750° C.; 700° C.; 650° C.; 600° C.; and 550° C. with ranges from any lower limit to any upper limit being contemplated.

Preferably, the pressure of the dehydrogenation process is from 0 psig to 1015 psig (0 kPag to 7000 kPag), 50 psig to 950 psig (345 kPag to 6550 kPag); from 100 psig to 900 psig (689 kPag to 6210 kPag) with ranges from any lower limit to any upper limit being contemplated.

The reactor configuration used for the dehydrogenation process generally comprises one or more fixed bed reactors containing a solid catalyst with a dehydrogenation function. Per-pass conversion of the saturated cyclic hydrocarbon (e.g., cyclohexane) using the present catalyst is typically greater than 70%, or greater than 80%, or greater than 90%, and typically at least 95%. Provision can be made for the endothermic heat of reaction, preferably by multiple adiabatic beds with interstage heat exchangers. The temperature of the reaction composition drops across each catalyst bed, and then is raised by the heat exchangers. Preferably, 3 to 5 beds are used, with a temperature drop of 30° C. to 100° C. across each bed. Preferably, the last bed in the series runs at a higher exit temperature than the first bed in the series.

Preferably, the alpha value of the dehydrogenation catalyst is from 0 to 10, and from 0 to 5, and from 0 to 1. The alpha value of the support is an approximate indication of the catalytic cracking activity of the catalyst compared to a standard catalyst. The alpha test gives the relative rate constant (rate of normal hexane conversion per volume of catalyst per unit time) of the test catalyst relative to the standard catalyst which is taken as an alpha of 1 (Rate Constant=0.016 sec .sup.-1). The alpha test is described in U.S. Pat. No. 3,354,078 and in J. Catalysis, 4, 527 (1965); 6, 278 (1966); and 61, 395 (1980), to which reference is made for a description of the test. The experimental conditions of the test used to determine the alpha values referred to in this specification include a constant temperature of 538° C., and a variable flow rate as described in detail in J. Catalysis, 61, 395 (1980). In other embodiments, the alpha value lower limit may be 0.0, 0.1, 0.2, 0.3, 0.4, 0.5, 0.6, 0.7, 0.8, 0.9, 1, 2, 3, 4, 5, 6, 7, 8, 9, and 10; and the upper alpha value limit may be 200, 175, 150, 125, 100, 90, 80, 70, 60, 50, 40, 30, 20, 10, 5, 1.9, 1.8, 1.7, 1.6, 1.5, 1.4, 1.3, 1.2, 1.1, 1, 0.9, 0.8, 0.7, 0.6, and 0.5 with ranges from any lower limit to any upper limit being contemplated.

Although the present process can be used with any composition comprising a saturated cyclic hydrocarbon (e.g., cyclohexane) and, optionally a five-membered ring compound (e.g., methylcyclopentane), the process has particular application as part of an integrated process for the conversion of benzene to phenol. In such an integrated process the benzene is initially converted to cyclohexylbenzene by any conventional technique, including alkylation of benzene with cyclohexene in the presence of an acid catalyst, such as zeolite beta or an MCM-22 family molecular sieve, or by oxidative coupling of benzene to biphenyl followed by hydrogenation of the biphenyl. However, in practice, the cyclohexylbenzene is generally produced by contacting the benzene with hydrogen under hydroalkylation conditions in the presence of a hydroalkylation catalyst whereby the benzene undergoes the following reaction (1) to produce cyclohexylbenzene (CHB):

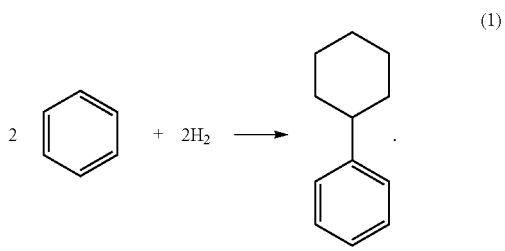 [SMILES: c1ccccc1 ; c1ccc(C2CCCCC2)cc1]

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between 100° C. and 400° C., such as between 125° C. and 250° C., while suitable reaction pressures are between 100 kPa and 7,000 kPa, such as between 500 kPa and 5,000 kPa. Suitable values for the molar ratio of hydrogen to benzene are between 0.15:1 and 15:1, such as between 0.4:1 and 4:1 for example, between 0.4 and 0.9:1.

The catalyst employed in the hydroalkylation reaction is generally a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325); PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in International Patent Publication No. WO97/17290); MCM-36 (described in U.S. Pat. No. 5,250,277); MCM-49 (described in U.S. Pat. No. 5,236,575); MCM-56 (described in U.S. Pat. No. 5,362,697); UZM-8 (described in U.S. Pat. No. 6,756,030); and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between 0.05 wt % and 10 wt %, such as between 0.1 wt % and 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from 1.5 to 1500, for example, from 75 to 750, such as from 100 to 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from, but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia.

The hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally 350 kPa to 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

The catalyst may comprise a binder. Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins, commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Although the hydroalkylation step is highly selective towards cyclohexylbenzene, the effluent from the hydroalkylation reaction will normally contain unreacted benzene feed, some dialkylated products, and other by-products, particularly cyclohexane, and methylcyclopentane. In fact, typical selectivities to cyclohexane and methylcyclopentane in the hydroalkylation reaction are 1-25 wt % and 0.1-2 wt % respectively.

In one embodiment, the dehydrogenation reaction is performed on all or a portion of the output of the hydroalkylation step.

In another embodiment, the hydroalkylation reaction effluent is separated into at least a (i) C6-rich composition; and (ii) the remainder of the hydroalkylation reaction effluent. When a composition is described as being "rich in" in a specified species (e.g., C6-rich, benzene-rich or hydrogen-rich), it is meant that the wt % of the specified species in that composition is enriched relative to the feed composition (i.e., the input). A "$C_6$" species generally means any species containing 6 carbon atoms.

Given the similar boiling points of benzene, cyclohexane, and methylcyclopentane, it is difficult to separate these materials by distillation. Thus in one embodiment, a $C_6$-rich composition comprising benzene, cyclohexane, and methylcyclopentane may be separated by distillation from the hydroalkylation reaction effluent. This $C_6$-rich composition may then be subjected to the dehydrogenation process described above such that at least a portion of the cyclohexane in the composition is converted to benzene and at least a portion of the methylcyclopentane is converted to linear and/or branched paraffins, such as 2-methylpentane, 3-methylpentane, n-hexane, and other hydrocarbon components such as isohexane, $C_5$ aliphatics, and $C_1$ to $C_4$ aliphatics. The dehydrogenation product composition may then be fed to a further separation system, typically a further distillation tower, to divide the dehydrogenation product composition into a benzene-rich stream and a benzene-depleted stream. The benzene-rich stream can then be recycled to the hydroalkylation step, while the benzene-depleted stream can be used as a fuel for the process. When a composition is described as being "depleted in" a specified species (e.g., benzene-depleted), it is meant that the wt % of the specified species in that composition is depleted relative to the feed composition (i.e., the input).

After separation of the $C_6$-rich composition, the remainder of hydroalkylation reaction effluent may be fed to a second distillation tower to separate the monocyclohexylbenzene product (e.g., cyclohexylbenzene) from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene may be effected in a transalkylation reactor, separate from the hydroalkylation reactor, over a suitable transalkylation catalyst, including large pore molecular sieves such as a molecular sieve of the MCM-22 family, zeolite beta, MCM-68 (see U.S. Pat. No. 6,014,018), zeolite Y, zeolite USY, and mordenite. A large pore molecular sieve has an average pore size in excess of 7 Å in some embodiments or from 7 Å to 12 Å in other embodiments. The transalkylation reaction is typically conducted under at least partial liquid phase conditions, which suitably include a temperature of 100 to 300° C., a pressure of 800 to 3500 kPa, a weight hourly space velocity of 1 to 10 $hr^{-1}$ on total feed, and a benzene/dicyclohexylbenzene weight ratio of 1:1 to 5:1. The transalkylation reaction effluent can then be returned to the second distillation tower to recover the additional monocyclohexylbenzene product produced in the transalkylation reaction.

After separation in the second distillation tower, the cyclohexylbenzene is converted into phenol by a process similar to the Hock process. In this process, the cyclohexylbenzene is initially oxidized to the corresponding hydroperoxide. This is accomplished by introducing an oxygen-containing gas, such as air, into a liquid phase containing the cyclohexylbenzene. Unlike the Hock process, atmospheric air oxidation of cyclohexylbenzene, in the absence of a catalyst, is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N"-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between 70° C. and 200° C., such as 90° C. to 130° C., and a pressure of 50 kPa to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

The another reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of 20° C. to 150° C., such as 40° C. to 120° C., a pressure of 50 kPa to 2,500 kPa, such as 100 kPa to 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid, and p-toluenesulfonic acid. Ferric chloride, boron trifluoride, sulfur dioxide, and sulfur trioxide are also effective homogeneous cleavage catalysts. The preferred homogeneous cleavage catalyst is sulfuric acid, with preferred concentrations in the range of 0.05 wt % to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

The effluent from the cleavage reaction comprises phenol and cyclohexanone in substantially equimolar amounts and, depending on demand, the cyclohexanone can be sold or can be dehydrogenated into additional phenol. Any suitable dehydrogenation catalyst can be used in this reaction, such as the dehydrogenation catalyst or a variation of the catalyst described herein. Suitable conditions for the dehydrogenation step comprise a temperature of 250° C. to 500° C. and a pressure of 0.01 atm to 20 atm (1 kPa to 2030 kPa), such as a temperature of 300° C. to 450° C. and a pressure of 1 atm to 3 atm (100 kPa to 300 kPa).

The invention will now be more particularly described with reference to the following non-limiting Examples and the accompanying drawings.

EXAMPLE 1

Dehydrogenation of Cyclohexane

A first dehydrogenation catalyst comprising 1 wt % platinum and 0.15 wt % tin on a silicon oxide support and a second dehydrogenation catalyst (comparative) comprising 1 wt % platinum and 1 wt % potassium on a silicon oxide support were crushed to 60/100 mesh and loaded into ½" (1.27 cm) outer diameter (OD) tubular downflow reactors. The catalysts were then separately contacted with a composition comprising 89 wt % benzene, 10 wt % cyclohexane and 1 wt % methylcyclopentane under dehydrogenation conditions of 480° C., 0.689 MPa, 10 hr$^{-1}$ weight hourly space velocity (WHSV), and a molar ratio of hydrogen to hydrocarbon ($H_2$/HC) of 4. As illustrated in FIG. 1, the Pt/Sn/$SiO_2$ catalyst achieved significantly higher cyclohexane conversion and selectivity than the Pt/K/$SiO_2$ catalyst.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A dehydrogenation process comprising:
   contacting a composition comprising at least 50 wt % of benzene and at least 0.1 wt % of cyclohexane, the wt % s based upon total weight of the composition, with a dehydrogenation catalyst having oxygen chemisorption value of greater than 30%, said dehydrogenation catalyst comprising:
   (i) 0.05 to 0.5 wt % of tin; (ii) 0.1 to 2 wt % of a metal selected from Groups 6 to 10 of the Periodic Table of the Elements, and (iii) a support, the wt % s based upon total weight of the dehydrogenation catalyst, wherein the dehydrogenation catalyst is prepared by sequential impregnation with the tin being applied to the support before the metal selected from Groups 6 to 10 of the Periodic Table of the Elements, and further wherein the dehydrogenation catalyst contains no cobalt.

2. The process of claim 1, wherein the composition comprises at least 1 wt % of cyclohexane, the wt % based upon total weight of the composition.

3. The process of claim 1, wherein the dehydrogenation catalyst converts at least 70% of the cyclohexane to benzene.

4. The process of claim 1, wherein the dehydrogenation catalyst comprises 0.1 to 0.5 wt % of the metal selected from Groups 6 to 10 of the Periodic Table of Elements, based upon total weight of the dehydrogenation catalyst.

5. The process of claim 1, wherein the metal selected from Groups 6 to 10 of the Periodic Table of Elements is platinum or palladium.

6. The process of claim 1, wherein the dehydrogenation process is conducted under dehydrogenation conditions comprising a temperature between 200° C. and 550° C. and a pressure between 100 kPa and 7,000 kPa.

7. The process of claim 1, wherein the composition further comprises at least 0.01 wt % methylcyclopentane, based upon total weight of the composition.

8. The process of claim 1, wherein the dehydrogenation catalyst comprises a support containing one or more of silica, alumina, a silicate, an aluminosilicate, zirconia or carbon.

9. The process of claim 1, wherein the dehydrogenation catalyst comprises a support containing an inorganic oxide selected from silicon dioxide, titanium dioxide and zirconium oxide.

10. A dehydrogenation process comprising:
    (a) providing a composition comprising at least 0.1 wt % of cyclohexane and at least 0.05 wt % of methylcyclopentane; and
    (b) producing a dehydrogenation reaction product by contacting at least a portion of the composition with a dehydrogenation catalyst under conditions effective to convert: (i) at least a portion of the cyclohexane to benzene; and (ii) at least a portion of the methylcyclopentane to at least one paraffin,
    wherein the dehydrogenation catalyst has oxygen chemisorption value of greater than 30%, and comprises: (i) 0.05 wt % to 0.5 wt % of tin; (ii) 0.1 wt % to 2 wt % of a metal selected from Groups 6 to 10 of the Periodic Table of the Elements, and (iii) a support, the wt % s based upon total weight of the dehydrogenation catalyst, further wherein the dehydrogenation catalyst contains no cobalt, and further wherein the dehydrogenation catalyst is produced by a method comprising
  (i) treating the support with the Group 14 metal to form a treated support;
  (ii) calcining the treated support at a temperature of 100° C. to 700° C.;
  (iii) impregnating the support with the Group 6 to 10 metal to form an impregnated support; and
  (iv) calcining the impregnated support at a temperature of 100° C. to 700° C.,
  wherein the impregnating step (iii) is effected after the treating step (i).

11. The process of claim 10, wherein the metal selected from Groups 6 to 10 of the Periodic Table of Elements is platinum or palladium.

12. The process of claim 10, wherein the impregnating step (iii) is effected after the calcining step (ii).

13. The process of claim 10, wherein the calcining step (iv) is conducted in an oxygen-containing atmosphere at a temperature of 200° C. to 500° C. for a time of 1 to 10 hours.

14. The process of claim 10, wherein the cyclohexane is present in an amount of at least 5 wt %, based upon total weight of the composition.

15. The process of claim 10, wherein the methylcyclopentane is present in an amount of at least 0.1 wt %, based upon total weight of the composition.

16. A process for producing cyclohexylbenzene, the process comprising:

(a) contacting benzene and hydrogen in the presence of a hydroalkylation catalyst under hydroalkylation conditions effective to form a hydroalkylation reaction product comprising cyclohexylbenzene, cyclohexane, methylcyclopentane, and benzene;

(b) separating at least a portion of the hydroalkylation reaction product into (i) a first composition that is rich in at least one of benzene, cyclohexane, and methylcyclopentane; and (ii) a second composition that is rich in cyclohexylbenzene;

(c) contacting at least a portion of the first composition with a dehydrogenation catalyst under conditions effective to convert at least a portion of the cyclohexane to benzene, wherein the dehydrogenation catalyst has oxygen chemisorption value of greater than 30%, and comprises: (i) 0.05 to 0.5 wt % of tin; (ii) 0.1 to 2 wt % of a metal selected from Groups 6 to 10 of the Periodic Table of the Elements; (iii) a support; and (iv) no cobalt, the wt % s based upon total weight of the dehydrogenation catalyst, further wherein the dehydrogenation catalyst is prepared by sequential impregnation with the tin being applied to the support before the metal selected from Groups 6 to 10 of the Periodic Table of the Elements; and (d) recycling at least a portion of the benzene formed in step (c) to the contacting step (a).

17. The process of claim 10, wherein the impregnating step (iii) is effected prior to or at the same time as the calcining step (ii).

* * * * *